US00PP36895P2

(12) United States Plant Patent
Welford

(10) Patent No.: US PP36,895 P2
(45) Date of Patent: Aug. 19, 2025

(54) ***ILEX* PLANT NAMED 'Golden Hoogendoorn'**

(50) Latin Name: *Ilex crenata*
Varietal Denomination: Golden Hoogendoorn

(71) Applicant: Franklin B. Welford, Lucedale, MS (US)

(72) Inventor: Franklin B. Welford, Lucedale, MS (US)

( * ) Notice: Subject to any disclaimer, the term of this patent is extended or adjusted under 35 U.S.C. 154(b) by 0 days.

(21) Appl. No.: 18/738,496

(22) Filed: Jun. 10, 2024

(51) Int. Cl.
*A01H 5/00* (2018.01)
*A01H 6/00* (2018.01)

(52) U.S. Cl.
USPC ..... Plt./247
CPC ..... *A01H 6/00* (2018.05)

(58) Field of Classification Search
USPC ..... Plt./247
CPC ..... A01H 5/00
See application file for complete search history.

*Primary Examiner* — Kent L Bell
(74) *Attorney, Agent, or Firm* — C. Anne Whealy

(57) ABSTRACT

A new and distinct *Ilex* plant named 'Golden Hoogendoorn', characterized by its relatively compact, upright to outwardly spreading and mounding plant habit; freely branching habit; dense and bushy growth habit; semi-glossy leaves that are initially yellowish green in color becoming darker green with development; and relative tolerance to high temperature and high humidity conditions.

1 Drawing Sheet

Botanical designation: *Ilex crenata.*
Cultivar denomination: 'GOLDEN HOOGENDOORN'.

BACKGROUND OF THE INVENTION

The present Invention relates to a new and distinct *Ilex* plant, botanically known as *Ilex crenata* and hereinafter referred to by the name 'Golden Hoogendoorn'.

The new *Ilex* plant is a naturally-occurring branch mutation of *Ilex crenata* 'Hoogendoorn', not patented. The new *Ilex* plant was discovered and selected by the Inventor on a single plant of 'Hoogendoorn' within a population of plants of 'Hoogendoorn' in a controlled environment in Lucedale, Mississippi on Oct. 11, 2016.

Asexual reproduction of the new *Ilex* plant by vegetative cuttings in a controlled environment in Lucedale, Mississippi since Feb. 8, 2017 has shown that the unique features of this new *Ilex* plant are stable and reproduced true to type in successive generations.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Golden Hoogendoorn'. These characteristics in combination distinguish 'Golden Hoogendoorn' as a new and distinct *Ilex* plant:

1. Relatively compact, upright to outwardly spreading and mounding plant habit.
2. Freely branching habit; dense and bushy growth habit.
3. Semi-glossy leaves that are initially yellowish green in color becoming darker green with development.

4. Relatively tolerant to high temperature and high humidity conditions.

Plants of the new *Ilex* differ from plants of the mutation parent, 'Hoogendoorn', primarily in developing leaf color as leaves of plants of the new *Ilex* are initially yellowish green in color whereas leaves of 'Hoogendoorn' are initially medium green in color. In addition, plants of the new *Ilex* are more tolerant to high temperature and high humidity conditions than plants of 'Hoogendoorn'.

Plants of the new *Ilex* can be compared to plants of *Ilex crenata* 'Adorned', not patented. Plants of the new *Ilex* differ from plants of 'Adorned', primarily in landscape performance as plants of the new *Ilex* are more tolerant to high temperature and high humidity conditions than plants of 'Adorned'.

BRIEF DESCRIPTION OF THE PHOTOGRAPH

The accompanying colored photograph illustrates the overall appearance of the new *Ilex* plant. The photograph shows the colors as true as it is reasonably possible to obtain in colored reproductions of this type. Colors in the photograph may differ slightly from the color values cited in the detailed botanical description, which accurately describe the colors of the new *Ilex* plant.

The photograph is a side perspective view of a typical plant of 'Golden Hoogendoorn' grown in a container.

DETAILED BOTANICAL DESCRIPTION

The aforementioned photographs and following observations and measurements describe plants grown during the spring and summer in three-gallon containers in an outdoor nursery in Park Hill, Oklahoma and under cultural practices typical of commercial *Ilex* production. During the production of the plants, day temperatures averaged 33° C. and night temperatures averaged 21° C. Plants were 30 months old when the photograph and detailed description were taken. In the following description, color references are made to The Royal Horticultural Society Colour Chart, 2015 Edition, except where general terms of ordinary dictionary significance are used.

Botanical classification: *Ilex crenata* 'Golden Hoogendoorn'.

Parentage: Naturally-occurring branch mutation of *Ilex crenata* 'Hoogendoorn' not patented.

Propagation:

*Type*.—By vegetative (softwood) cuttings.

*Time to initiate roots, winter*.—About 40 days at temperatures about 5° C.

*Time to produce a rooted young plant, winter*.—About four months at temperatures about 5° C.

*Root description*.—Fine, fibrous; typically brownish white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial shrub; relatively compact, upright to outwardly spreading and mounding plant habit; overall shape, flattened globular; moderately vigorous growth habit and moderate growth rate.

*Branching habit*.—Freely branching habit; dense and bushy growth habit with about 12 to 15 primary lateral branches developing per plant and secondary lateral branches developing potentially at every node.

*Plant height*.—About 29 cm.

*Plant diameter, area of spread*.—About 57.5 cm.

*Lateral branch description*.—Length: About 25 cm to 30 cm. Diameter: About 6 mm to 7 mm. Internode length: About 7 mm to 14 mm. Strength: Strong; when developing, flexible; developed, rigid and not flexible. Aspect: About 45° to 75° from vertical. Texture and luster: Developing branches: Smooth, glabrous; herbaceous; slightly glossy. Developed branches: Smooth, glabrous; woody, matte. Color: Developing branches: Close to 144A to 144B. Developed branches: Close to N200B and N200C.

*Leaf description*.—Arrangement: Alternate, simple. Length: About 12 cm to 18 cm. Width: About 6 mm to 9 mm. Shape: Oblanceolate. Apex: Acute to short cuspidate. Base: Cuneate with obtuse tendencies. Margin: Shallowly serrate. Venation pattern: Pinnate. Aspect: Mostly horizontal. Texture and luster, upper surface: Smooth, glabrous; semi- glossy. Texture and luster, lower surface: Smooth, glabrous; slightly glossy. Color: Developing leaves, upper surface: Close to N144B and 145A; occasionally with random segments, close to 147B. Developing leaves, lower surface: Close to N144B and 145A. Fully expanded leaves, upper surface: Close to 147A; venation, close to 144B. Fully expanded leaves, lower surface: Close to 147B; venation, close to 144B. Petioles: Length: About 9 mm. Diameter: About 0.5 mm. Strength: Strong; flexible. Texture and luster, upper and lower surfaces: Smooth, glabrous; slightly glossy. Color, upper and lower surfaces: Close to 144B.

Flower description: To date, flower initiation and development have not been observed on plants of the new *Ilex* plant.

Garden performance: Plants of the new *Ilex* have been observed to have good garden performance and to be tolerant to rain, wind, high humidity and temperatures ranging from about −20° C. to 43° C.

Pathogen & pest resistance: To date, plants of the new *Ilex* have not been observed to be resistant to pathogens and pests common to *Ilex* plants.

It is claimed:

1. A new and distinct *Ilex* plant named 'Golden Hoogendoorn' as herein illustrated and described.

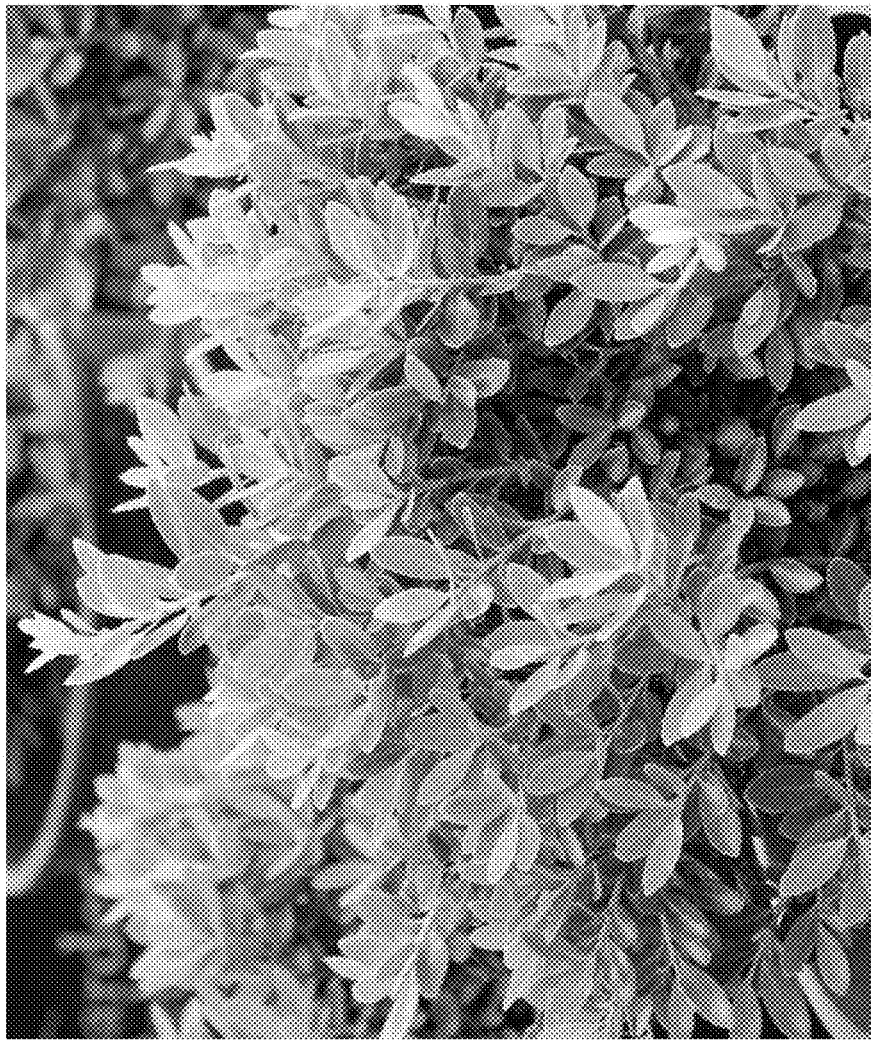

* * * * *